(12) United States Patent
Nordenhem et al.

(10) Patent No.: US 7,073,288 B2
(45) Date of Patent: Jul. 11, 2006

(54) PROTECTION OF TREE PLANTS

(75) Inventors: Henrik Nordenhem, Ostervala (SE); Goran Nordlander, Uppsala (SE)

(73) Assignee: Robigus AB, Stockholm (SE)

( * ) Notice: Subject to any disclaimer, the term of this patent is extended or adjusted under 35 U.S.C. 154(b) by 0 days.

(21) Appl. No.: 10/490,099

(22) PCT Filed: Sep. 19, 2002

(86) PCT No.: PCT/SE02/01693

§ 371 (c)(1),
(2), (4) Date: Mar. 19, 2004

(87) PCT Pub. No.: WO03/024216

PCT Pub. Date: Mar. 27, 2003

(65) Prior Publication Data

US 2004/0244287 A1    Dec. 9, 2004

(30) Foreign Application Priority Data

Sep. 20, 2001  (SE) .................................... 0103157

(51) Int. Cl.
*A01G 13/00* (2006.01)
(52) U.S. Cl. ...................................... 47/32.6
(58) Field of Classification Search .............. 47/8, 47/23.1, 23.2, 32.4, 32.6; 43/108, 107
See application file for complete search history.

(56) References Cited

FOREIGN PATENT DOCUMENTS

| | | | |
|---|---|---|---|
| DE | 36 41 680 A1 | | 6/1998 |
| EP | 0 903 081 A1 | | 3/1999 |
| JP | 61-28 6302 A | | 12/1986 |
| SE | 7711141 A | | 4/1979 |
| SE | 7711141 | * | 5/1979 |
| WO | WO 95/32620 A1 | | 12/1995 |
| WO | WO 02/065837 A1 | | 8/2002 |

OTHER PUBLICATIONS

Eidmann et al. *Stockings For Protection Of Containerized Conifer Seedlings Against Pine Weevil (Hylobius abietis L.) Damage*, Scand J. For. Res., vol. 4, pp. 537-547, 1989.
Eidmann et al., *Physical Protection Of Conifer Seedlings Against Pine Weevil Feeding*, Scand J. For. Res., vol. 11, pp. 68-75, 1996.
Hagner et al., *Survival After Planting Without Soil Preparation For Pine And Spruce Seedlings Protected From Hylobius abietis By Physical And Chemical Shelters*, Scand. J. For. Res., vol. 10, pp. 225-234, 1995.
Lindstrom et al., *Field Performance Of A Protective Collar Against Damage By Hylobius abietis*, Scand. J. For. Res., vol. 1, pp. 3-15, 1986.
Orlander et al., *Mekaniska Syntbaggeskydd*, K. Skogs-o Lantbr.akad. Tidskr., vol. 137, pp. 43-50, 1998.
Petersson et al., *Falttest Av Mekaniska Snytbaggeskdd For Tackrotsplantor- Forosk Anlagt Varen 1997, Reviderat Hosten 1997*, Sveriges Lantbruksuniversitet, Field trial, ASA Forest Research Station, Swedish University Of Agri. Sci., Lanmbrult, vol. 3, pp. 1-17, 1998.
Peterson et al., *Mekaniska Syntbaggeskydd For Barrot- och Tackrotsplantor- Forsok Anlagt Varen 1996, Reviderat Hosten 1996 Och 1997*, Sveriges Lantbruksuniversitet, Field trial, ASA Forest Research Station, Swedish University Of Agri. Sci., Lanmbrult, vol. 3, pp. 1-13, 1998.
Von Hofsten et al., *Mekaniska Snytbaggeskydd-En Lagesrapport*, vol. 24, pp. 1-6, 1999.

* cited by examiner

*Primary Examiner*—T. Nguyen
(74) *Attorney, Agent, or Firm*—Browdy and Neimark, PLLC

(57) ABSTRACT

The present invention relates to a formulation with particles of a controlled particle size distribution, fixed in an elastic coating, that is applied, either separately or in mixture, in order to prevent attacks by gnawing animals, especially insects, to seedlings.

19 Claims, No Drawings

PROTECTION OF TREE PLANTS

TECHNICAL FIELD

The present invention relates to a formulation intended for protection of tree plants and a method of applying said formulation on tree plants.

BACKGROUND OF THE INVENTION

Reforestation is a necessary, and in several countries by law prescribed method to achieve a sustainable forestry. One method is to leave selected seed-trees on the clear-cutting, another to plant seedlings after different kinds of soil preparation. The methods can be used in combination. Planting of seedlings is used to assure that a certain plant density is achieved on the regeneration area.

Many dangers, e.g. drought and attacks from wild animals and insects, threaten the development of a managed forest stand. A high rate of survival of the plants means reduced costs for the reforestation and increased future income.

Attacks from insects are very costly for the forest industry. Treatment of seedlings with insecticide (permethrin) will not be allowed in the European Union in the future. In spite of the fact that a ban has been proposed for several years, permethrin is still allowed for use, since the economic consequences of a ban has been regarded as insurmountable for the forest industry.

Coniferous seedlings are often treated with permethrin in the plant nursery before sale. The treatment of the plant with permethrin is often repeated in the field the following year. The treatment with permethrin is thus connected with increased costs in addition to the initial costs.

A great number of methods for reducing plant damage without using permethrin have been invented and developed. These methods have been assessed in both field tests and laboratory examinations (Lindström et al 1986, Eidmann & Sydow 1989, Eidmann et al. 1996, Hagner & Jonsson 1995, Hofsten et al. 1999,).

THE STATE OF THE ART

A number of mechanical devices have been used in order to exclude pine weevils and other insects. One series of devices can be described as cases of different geometrical shapes, e.g. cylinders or cones. They are applied manually or by mechanical devices around the tree plant. Other inventions aim at coating the stem of the plant with a latex or dispersion, that prevents gnawing by the pine weevil. According to the Swedish patent 9901062-1 a dispersion is mixed with a gnaw-reducing substance in order to make the coating unpalatable. The known inventions have several disadvantages, that have been revealed in field trials. The mechanical devices, made as casings, often do not remain in place for a longer period of time and cannot offer the intended durable protection of the plant. Various types of coatings of the plant display poor protection, sometimes noticed already in the first year, by the insects' gnawing and removal of the protective coating in order to reach the attractive plant bark. Admixture of gnaw-reducing substances in a latex or coating layer prevents the pine weevil to gnaw away the coating. However, the gnaw-reducing substances are expensive and in some cases reduce the vigour of the tree-plant.

A suggestion to use glue and sand, of a not known specification, can be considered to be included among mechanical devices to reduce the pine weevil's gnawing on tree-plants. The suggestion was evaluated in two field trials, conducted in the spring 1996 and 1997 at the Asa Forest Research Station, the Swedish University of Agricultural Sciences, Lammhult. The test results showed that plants treated according to the suggestion and untreated plants had approximately the same degree of damage by gnawing. (Pettersson & Örlander 1998a, 1998b).

The method of treatment of the plants was described in the trial report: "Glue+sand is a two step treatment. Glue is first applied to the lower part of the plant stem, then sand is sprayed to the glue-treated part of the stem". No specifications of the glue and sand are given in the reports. In the trials of 1996 the protected part of the stem was 9 cm, in 1997 the protected stem was, on average, 12.6 cm from the root.

The field trial that started in 1996 was finally evaluated after two seasons. 91% of the plants, treated with glue+sand were dead or severely damaged by the gnawing of pine weevils. In comparison, 94% of the untreated plants were dead or damaged, and 14% of the plants treated twice with permethrin were dead or severely damaged. The level of attack was high on the test site, but it was conclusively stated in the report that the protective effect of glue+sand was completely insufficient.

The protective effect of the glue+sand preparations was revealed to be very low also in the 1997 trials. 82% of the treated plants were dead or severely damaged after the first season, while 90% of the untreated plants were dead or damaged. It was verified that the glue+sand method of treatment was completely insufficient.

The almost non-existing protection offered by glue+sand is clearly described in a paper, which summarises conclusions from 15 years of field trials of various protective devices for tree plants. (Örlander 1998).

The mouth opening at the apex of the snout of the pine weevil is equipped with a pair of gnawing tools, the mandibles. They are used to gnaw and bite away the outer bark and other inedible matter on the plant's stem. The mandibles and snout are also used to pry away unwanted material, which covers the desired inner bark. The gap or the distances between the mandibles in open position is about 0.5 mm. Uncovering of edible plant material is a part of the pine weevil's natural behaviour. It implies that sand on bark in general is easily pried or bitten away by the pine weevil. This may be the main cause to the negative field trials results, referred to above.

DETAILED DESCRIPTION OF THE INVENTION

The present invention refers to a formulation, defined in claim 1, and a method to protect tree plants, defined in claim 9.

Surprisingly, if a particulate material is selected, with a particle size distribution so that the particles cannot be bitten away without damaging the mouthpieces or mandibles and at the same time so small so insufficient leverage is obtained when prying (i.e. they cannot be pried loose), a sufficient protection against gnawing is obtained. The particles must be distributed on the covered or coated surface, so that the principal distance between two particles is less than the width of the pine weevil's snout. Then the snout cannot be inserted between two particles. The particles are fixed in an elastic coating (binder), characterised by its ability to adhere to the particles and the plant stem during a long period of time, preferably not less than two years. The coating is further characterised by its ability to expand corresponding to at least two years of growth without crack formation. This implies that the coating's expansion at failure exceeds 100%, i.e. it has an elongation at break higher than 100%.

By applying such a formulation with coating and particles with adapted properties, as described above, pine weevils surprisingly refrain from attacking the tree plant. Instead, the weevils then feed on other easily available roots and twigs of larger trees, thereby causing no damage of economic importance.

The particulate material is an inorganic material having a narrow particle size distribution with a mean particle diameter preferably in the range 0.1 to 0.5 mm.

The shape of the particles can be selected according to various strategies. Round, even particles, that are difficult to catch by the mandibles or sharp, angular, made of e.g. glass pearls, carborundum, sand, filings or glass fibres, calcinated clay materials, such as Leca particles, mineral particles such as mica, vermiculite, dolomite and quartz particles, and rock particles such as pumice and perlite particles, can be utilised. The particles can have such a length/diameter ratio that the particles are rather classified as fibres. Fibres or filings can, by use of magnetism or electrostatic forces, be orientated so that the sharp edges are shown towards the weevil. Surprisingly, biting away or prying loose is rendered more difficult in comparison to a randomly selected particle distribution and orientation.

The particles are present in the binder in such an amount that the distance between the particles does not exceed 2 mm.

The coating is selected so that the adhesion properties and elasticity corresponds to the desired function. It is obvious that the properties of the formulation shall admit a simple and automated application on the plants.

The man, skilled in the art, realises that the coating can be applied separately on the plant and covered with particles during the coating's open time. Hence, particles that do not adhere can be reclaimed and reused.

The method can also be performed by mixing particles into the coating prior to the application on the plant. By adjusting the surface tension of the formulation, the edges of the particles can be exposed in a sufficiently unpleasant manner to the weevils, without giving them opportunity to bite away or pry loose the particles. The formulation may also prevent other gnawing insects and mammals, e.g. voles, rodents, rabbits, hares and deer, to feed on the plants.

The particles are selected so that the mean particle size interval is 0.1–0.5 mm.

It is obvious that particles and coating components are selected so they are not unpleasant or harmful to man and plants.

The coating is produced from known components which provide the desired elasticity and adhesion, either singly or as a mixture such as polymer or copolymer dispersions, e.g. polyacrylates, resins, alkyds, polysaccharides and their derivatives, proteins, including modified or derivatives. The dispersions can also include other components such as abietic acid derivatives, oils and fats, drying and non-drying, paraffins, e.g. paraffin wax, surfactants etc. in order to facilitate e.g. the application of the formulation to the plant and to facilitate the incorporation of gnaw inhibiting substances into the formulation. Furthermore, the coating can be protected against degradation, primarily from UV-light and moisture, by admixing pigments into the formulation, preferably reflective or bright pigments, e.g. of aluminium or titanium dioxide also in view of the fact that pine weevils avoid bright surfaces.

It is obvious for the man, skilled in the art, to select combinations of coating components and particles that yields the lowest cost for the final formulation and for the treated tree plant at a desired survival rate.

The following examples are provided in order to illustrate the invention but is not intended to delimit the scope of protection of the invention in any way.

EXAMPLE 1

Field Trial with Treated Plants

A coating, with the composition given in Table 2, was applied to tree plants. Particles, size predominately between 0,2–0,5 mm, 50% by volume, were spread on the open composition. The plants were planted at three sites in the county of Småland, Sweden 2002. At each site 50 plants of each treatment were planted in a randomised block design. The data from the three sites were pooled; i.e. each treatment is represented by 150 plants. Plants used were containerised Norway spruce seedlings. The field trial was planted on fresh clear-cuttings 21–24 May and was evaluated 27–30 August. The trial showed a very good protection against weevil attacks during the growing season (Table 1). The comparison with permethrin shows that the protection is even better than with the insecticide currently used in forestry.

The field trial also revealed a very good durability of the applied treatment, since 99% of the seedlings had an intact coating at the end of the season. Therefore it is likely that the coating will protect the seedlings well a second season. A coating according to previously known technology was also tested, i.e. the commercially available product Hylobex (Göldner). It is obvious from the results in Table 1 that the formulations according to the present invention give much better protective effect than Hylobex.

TABLE 1

Field trial with Norway spruce plants, treated with particles, spread on coating C (see Table 2), applied to the lower half of the plant stem. Control treatments included plants treated with the insecticide permethrin, untreated plants, and treated with a commercially available formulation Hylobex (Göldner).

| Treatment | Mean gnawing area on lower part of stem (%) | Plants killed by pine weevils (%) | Status of protection; % intact |
|---|---|---|---|
| Coating C + sand particles | 0 | 3 | 93 |
| Coating C + Leca particles | 1 | 8 | 99 |
| Permethrin | 12 | 2 | |
| Untreated | 60 | 72 | |
| Known technology: Hylobex | 38 | 37 | 7 |

TABLE 2

Composition of coating C (weight %)

| Component | Coating C |
|---|---|
| Surfactant | 12 |
| Acrylic copolymer | 88 |

EXAMPLE 2

Field Trials with Treated Plants

A coating, by a composition given in Table 4, was applied to tree plants. Particles, size 0.2–0.5 mm, were spread on the open composition. The plants were planted in two field trials in the county of Uppland, Sweden 2001. Both trials were randomised block tests including 100 and 70 blocks respectively (one tree plant per treatment in each block) Plants used were containerised Norway spruce seedlings. Field trial 1 was planted on a fresh clear-cutting 31 May and was evaluated 20 September. Field trial 2 was planted one-year-old clear-cutting 23 August and was evaluated 14 Sep. 2001.

Trial 1 showed a very good protection against weevil attacks during the growing season. (Table 3), indicating a result that corresponds to the demands of forestry industry. Field trial 2 indicates an improved protection level of the particles on coating B in comparison to coating A. (Field trial 1 utilised only coating A). The results are surprising in the light of previously known technology.

TABLE 3

Field trials with Norway spruce plants, treated with particles, spread on a coating A and B (see Table 4), applied to the lower half of the plant stem. Control treatments included plants treated solely with coating A and B as well as untreated plants.

| Treatment | Attacked plants (%) | Girdled plants (%) |
|---|---|---|
| Trial 1 | | |
| Coating A + particles | 11.0 | 3.0 |
| Coating A | 62.0 | 40.0 |
| Untreated plants | 88.0 | 57.0 |
| Trial 2 | | |
| Coating A + particles | 4.2 | 1.4 |
| Coating B + particles | 0 | 0 |
| Coating B | 38.6 | 24.3 |
| Untreated plants | 42.9 | 21.4 |

TABLE 4

Composition of coating A and B (weight %)

| Component | Coating A | Coating B |
|---|---|---|
| Surfactant | 21 | 21 |
| Microcrystalline wax | 24 | — |
| Polyacrylate dispersion | 31 | 52 |
| Abietic acid derivative | 24 | 26 |
| Pigments | 1 | 1 |

REFERENCE

Eidmann, H. H. & Sydow, F. von, Hagner, M. 1989. Stockings for protection of containerised conifer seedlings against pine weevil (*Hylobius abietis*) damage. Scandinavian Journal of Forest Research 4: 537–547.

Eidmann, H. H., Nordenhem, H. & Weslien, J. 1996. Physical protection of conifer seedlings against pine weevil feeding. Scandinavian Journal of Forest Research 11: 68–75.

Jonsson, C. 1995. Survival after planting without soil preparation for pine and spruce seedlings protected from *Hylobius abietis* by physical and chemical shelters. Scandinavian Journal of Forest Research 10: 225–234.

Hofsten, H. von, Petersson, M. & Örlander, G. 1999. Mechanical devices for protection against pine weevil—a progress report. SkogForsk, Resultat 24: 1–6 (In Swedish with English summary).

Lindström, A., Hellqvist, C., Gyldberg, B., Långström, B. & Mattsson, A. 1986. Field performance of a protective collar against damage by *Hylobius abietis*. Scandinavian Journal of Forest Research 1: 3–15.

Petersson, M., & Örlander, G. 1998a. Mekaniska snytbaggeskydd för barrot-och täckrotsplantor—försök anlagt våren 1996, reviderat hösten 1996 och 1997. Asa försökspark, rapport 1998-2: 1–12.

Petersson, M. & Örlander, G. 1998b. Fälttest av mekaniska snytbaggeskydd för täckrotsplantor—försök anlagt våren 1997, reviderat hösten 1997. Asa försökspark, rapport 1998-3: 1–7.

Örlander, G. 1998. Mekaniska snytbaggeskydd. Kungliga Skogs och Lantbruksakademiens Tidskrift 137(15): 43–50.

The invention claimed is:

1. A formulation for protection of tree plants which comprises
    an inorganic particulate material of particles with a mean particle size within the range of 0.1 to 0.5 mm and an elastic binder material,
    said formulation when applied as a coating having an elongation at break larger than 100%,
    said formulation being adapted to adhere to both the plant bark,
    wherein the particles are applied in or on the binder material in such an amount that the distance between the particles does not exceed 2 mm when the formulation is applied as a coating.

2. A formulation according to claim 1 wherein the particulate material is sand.

3. A formulation according to claim 1 wherein the particulate material is calcinated clay.

4. A formulation according to claim 1 wherein the binder material comprises a polymer dispersion.

5. A formulation according to claim 1 which includes a pigment.

6. A formulation according to claim 5 wherein the pigment is selected from reflective or bright pigments.

7. A formulation according to claim 1 wherein the binder includes a surfactant.

8. A formulation according to claim 1 wherein at least one component of said formulation is adapted for protecting tree plants against attacks by pine weevil.

9. A method to protect a tree plant against gnawing by animals and insects, comprising
    providing a lower part of the plant with a coating comprising an elastic binder and an inorganic particulate material wherein the binder adheres both to the plant bark and to the particulate material and wherein particles of said particulate material have a mean particle size within the range 0.1 to 0.5 mm and are present in such an amount that the distance between the particles does not exceed 2 mm, said coating having an elongation at break higher than 100%.

10. A method according to claim 9 wherein the binder first is applied to the tree plant and then the particles are applied on the binder.

11. A method according to claim 9 wherein the particles first are mixed into the binder and then the formulation including the binder and the particulate material is applied on the plant.

12. A coating for protection of tree plants which comprises
   an inorganic particulate material of particles with a mean particle size within the range of 0.1 to 0.5 mm and an elastic binder,
   which coating has an elongation at break larger than 100%,
   wherein the binder adheres both the plant bark and the particles, and
   the particles being applied in or on the binder in such an amount that the distance between the particles does not exceed 2 mm.

13. A coating according to claim 12 wherein the particulate material is sand.

14. A coating according to claim 12 wherein the particulate material is calcinated clay.

15. A coating according to claim 12 wherein the binder material comprises a polymer dispersion.

16. A coating according to claim 12 which includes a pigment.

17. A coating according to claim 16 wherein the pigment is selected from reflective or bright pigments.

18. A coating according to claim 12 wherein the binder includes a surfactant.

19. A coating according to claim 12 wherein at least one component thereof is adapted for protecting tree plants against attacks by pine weevil, and said coating is on the stem of a tree plant.

* * * * *